(12) United States Patent
White

(10) Patent No.: US 6,283,751 B1
(45) Date of Patent: Sep. 4, 2001

(54) ANATOMICAL INTERPROXIMAL DENTAL STIMULATOR

(76) Inventor: Dennis J. White, 51 Nostrand Rd., Plainsboro, NJ (US) 08512

( * ) Notice: Subject to any disclaimer, the term of this patent is extended or adjusted under 35 U.S.C. 154(b) by 0 days.

(21) Appl. No.: 09/007,701

(22) Filed: Jan. 15, 1998

(51) Int. Cl.$^7$ ........................................... A61C 3/00
(52) U.S. Cl. .................... 433/141; 132/329; 15/167.1
(58) Field of Search ....................... 433/141, 216; 132/321, 329; 15/167.1, 167.2, 22.1, 176.4, 110

(56) References Cited

U.S. PATENT DOCUMENTS

| | | | | |
|---|---|---|---|---|
| 1,058,234 | * | 4/1913 | Hamilton | 132/321 |
| 3,896,824 | | 7/1975 | Thornton | 132/89 |
| 3,929,144 | | 12/1975 | Tarrson et al. | 132/93 |
| 4,011,658 | | 3/1977 | Tarrson et al. | 32/40 R |
| 4,319,377 | | 3/1982 | Tarrson et al. | 15/111 |
| 4,449,933 | * | 5/1984 | Forni | 433/141 |
| 4,450,849 | | 5/1984 | Cerceo et al. | 132/89 |
| 4,462,136 | * | 7/1984 | Nakao et al. | 132/321 X |
| 4,911,187 | | 3/1990 | Castillo | 132/321 |
| 5,609,170 | | 3/1997 | Roth | 132/329 |
| 5,704,388 | * | 1/1998 | Freeman | 132/329 |

OTHER PUBLICATIONS

Advisory statement—American Academy of Orthopedic Surgeons, 1997.

* cited by examiner

Primary Examiner—Nicholas D. Lucchesi

(57) ABSTRACT

A dental/gingival stimulating article is disclosed that provides interdental stimulation and plaque removal to the interproximal areas. This toothbrush like design holds bristle tips that terminate in a vee shaped design. The instrument is held in one hand and directed with appropriate direction and force to guide fiber ends into the spaces between the gum and teeth interproximally. Its vee shape will allow non-restricted passage around the interdental papilla. The rotational direction used on the handle will dissipate to a massaging motion within the sulci. Therefore, the threat of interproximal caries is reduced and the occurrence of periodontal disease is minimized.

3 Claims, 5 Drawing Sheets

FIG. 1
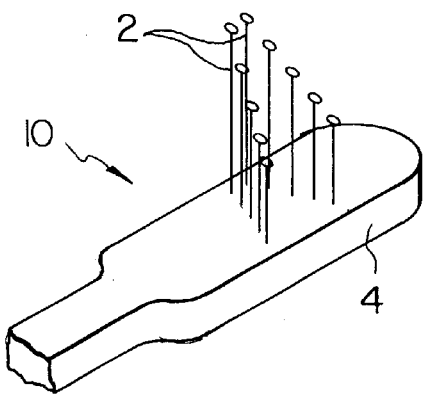
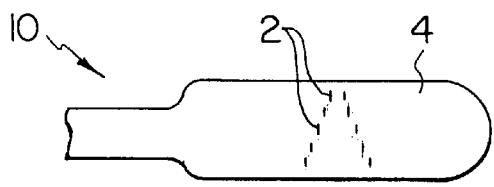
FIG. 2
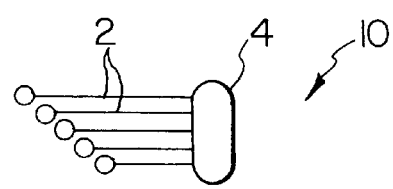
FIG. 3
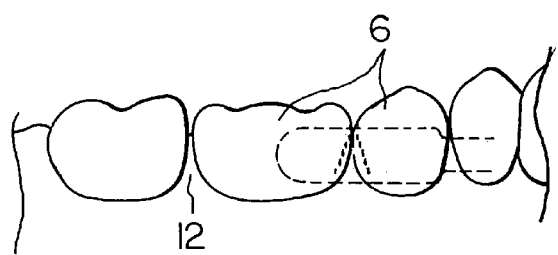
FIG. 4

ANATOMICAL INTERPROXIMAL DENTAL STIMULATOR

FIELD OF INVENTION

This invention relates a dental article to stimulate gums and clean teeth in interproximal areas, which is both efficient and easy to use.

BACKGROUND OF THE INVENTION

Regarding dental hygiene, it has been found desirable to remove residual food particles and plaque harboring between the teeth and under the gums. In fact, irritation occurs when food and plaque are left to remain between the teeth. This leads to tooth decay and periodontitis. Moderate to severe periodontitis will cause recession of gums, mobility of teeth, and eventual tooth loss. Teeth must be brushed and adjacent soft tissue massaged in order to maintain oral health.

Oral health is critical for certain individuals. Patients with heart defects are susceptible to further heart damage due to a bacteremia originating from inflamed gums. Orthopedic patients with total joint replacements are also candidates for similar infections due to unhealthy gums. An Advisory Statement of 1997 by the American Academy of Orthopaedic Surgeons strongly outlines the need for healthy oral tissues. Effective daily oral hygiene is important to all of us as well as in the above specificities.

A biomechanical problem exists with toothbrushing. There is a fine line between one keeping teeth adequately clean and one being overzealous and causing tooth abrasion and gingival recession from overbrushing. Harmful stress to oral tissues can be caused by a toothbrush on gingival tissue when an individual tries to reach deeper inaccessible areas between the teeth.

A normal toothbrush is effective for cleaning areas of the teeth exposed to the brush, but the professionals are in agreement that the bristles can not reach into deeper areas between the teeth. A favorable way to clean this interdental area is to use a length of string, commonly called dental floss. The intended motion of such floss is to have it seesaw through the contacts and be directed gently into the sulcus. It is then curved around the tooth, and lifted in the incisal direction while putting force toward the tooth surface being cleaned.

Unfortunately, flossing the entire dentition is time consuming. To accomplish this feat for all the teeth is very difficult. The back teeth must be done blindly, and many people don't have the dexterity to accomplish the task.

The interdental area is also maintained by interproximal brushes. However, in a normal and healthy interdental area, the space between the teeth is consumed by the dental papilla and this precludes the use of a small brush. The interdental brush is generally recommended by dentists to the older population.

Tooth picks and Johnson and Johnson's Stimudents are utilized to remove accessible plaque. However, they are too bulky to be placed into the delicate interdental sulcular area.

In U.S. Pat. No. 3,896,824 Thornton reveals a type of interdental massager that is an efficient type of dental floss. Difficulty arises when it is snapped through a tight contact. It is also arduous to clean an entire mouth at one time.

In U.S. Pat. No. 4,450,849 Cereo et al. disclose a type of dental tape or floss with rows of protuberances. This gingival stimulator suffers from inefficiency. It is very time consuming to place this type of device between each dental contact. Compliance on a regular basis could only be done by a very dedicated individual.

In U.S. Pat. No. 4,462,136 Nakao et al. invented a massaging device with small rows of fibers wrapped in a sheath. The converging shape of this stimulator makes for an inefficient design for entering into the narrow sulcular area and massaging epithelial lining.

In U.S. Pat. Nos. 3,929,144 and 4,011,658 Tarrson reveals a device for inserting dental floss through interproximal areas. This device is utilized to navigate a regular piece of dental floss between teeth. The device is not used to directly stimulate the gums. The loop end is utilized as an anchor to direct floss in a pulling motion.

In U.S. Pat. No. 4,319,377 Tarrson et al. disclose an interproximal toothbrush. The bristles of this invention are a cone design and this feature does not consider the space utilized by the interdental papilla. It is not an anatomical design.

In U. S. Pat. No. 4,911,187 Castillo designs a dental pick apparatus which is also of a symmetrical design. This brush does not allow for the space taken by the dental papilla.

In U.S. Pat. No. 5,609,170 Roth has invented an interproximal toothbrush. The extent of travel of the stimulator is limited by the length of the working sides. Because it is limited in its gingival reach by the highest part of epithelial attachment that it first touches, it is not free to splay into different directions. Areas of the interpoximal sulcus will not be stimulated.

OBJECTS AND ADVANTAGES

The object of this invention is to deliver efficiency in the area of gingival stimulation. The average person does not wish to take the time to floss between teeth. To do properly, it is very challenging and there is little feel better/look better reward afterward.

Flossing has a passive effect on the gums. It does not truly stimulate the gum since it is held against the teeth and there is not a strong contact to the soft tissue. Floss removes plaque from the teeth not the gums. Gingiva will remain healthy because nearby plaque is absent.

The stimulator of the present invention comes into intimate contact with the sulcular epithelium and has a direct role in massaging the gum. Because it feels good, this positive feedback encourages its use.

Also, the invention does not have to pass through an interproximal contact. The stimulator is passed from either the buccal or the lingual direction and circumvents the problem of entering through the contact.

The contact has always been a drawback to use of dental floss and yet this is not an area we are purposefully attempting to clean. The contact is self cleaning and is always free of plaque.

This disclosure differs from a toothbrush in that the tips or fibers are fewer in number. Consequently, the fibers have the ability to penetrate deeper. The force of a large number of bristles, as in toothbrushes used today, press against surrounding tooth and gingiva. Thus, the surrounding tissues prevent the necessary deeper stimulation interproximally and into the sulcus by the individual fibers. The surrounding areas may become damaged since they are overbrushed and even traumatized. Yet, the inaccessible areas suffer from lack of stimulation.

The anatomical arrangement of the bristle ends of this disclosure are designed to meet the specific shape of the interproximal area. The stimulator can be used on areas where there is no interproximal tissue loss. This is different from present day interproximal brushes, which are too bulky to enter healthy papillary areas with no recession.

BRIEF DESCRIPTION OF DRAWING

FIG. 1 is a lateral perspective view of an interproximal stimulator.

FIG. 2 is a frontal perspective of stimulator viewing directly down bristle ends.

FIG. 3. is an end view of interproximal stimulator.

FIG. 4 is a lateral view of stimulator juxtaposed to interproximal area.

DETAILED DESCRIPTION OF THE INVENTION

FIG. 1 represents an interproximal stimulator of the disclosed invention. Bristles, 2, are positioned near end of the toothbrush-like base, 4 to make the interproximal stimulator, 10.

The anatomical arrangement of the bristles allow for entry into the interproximal papillary area. FIG. 2 is a frontal view of disclosed stimulator and shows arrangement for the setting of stimulator bristles, 2. The fibers or bristles terminate free ends in a "V" or vee pattern. This frontal view connotation is assigned to that perspective of the stimulator that actually addresses the recipient, or worked upon, gingival area. In other words, frontal relates to that perspective of the stimulator that the teeth would see as it approaches the papillary area.

Figure 5:
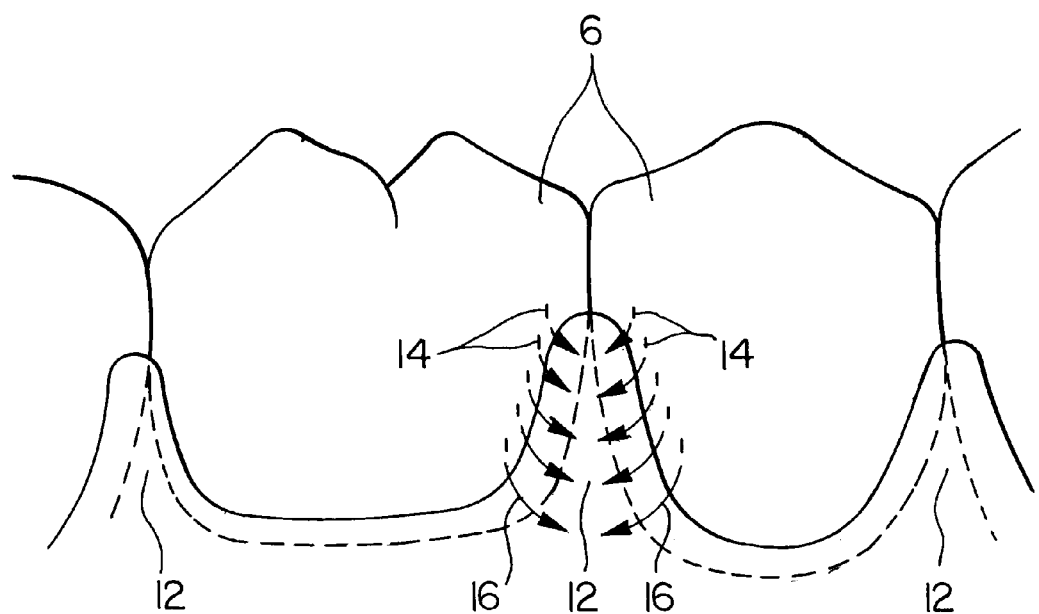
FIG. 5 is a lateral view of interproximal area showing path of entry of fibers.

The target placement of bristle tips is in the interproximal area, FIGS. 4 and 5. The vee pattern of bristle ends corresponds to the shape of the interdental papilla, 12. In FIG. 5, point contacts, 14 on the teeth, 6 are made by ends of bristles of stimulator. The arrows, 16, demonstrate path of movement of bristle tips as they progress into the sulcus. The natural curves of the teeth help direct movement into the desired sulcular area.

Figure 6:
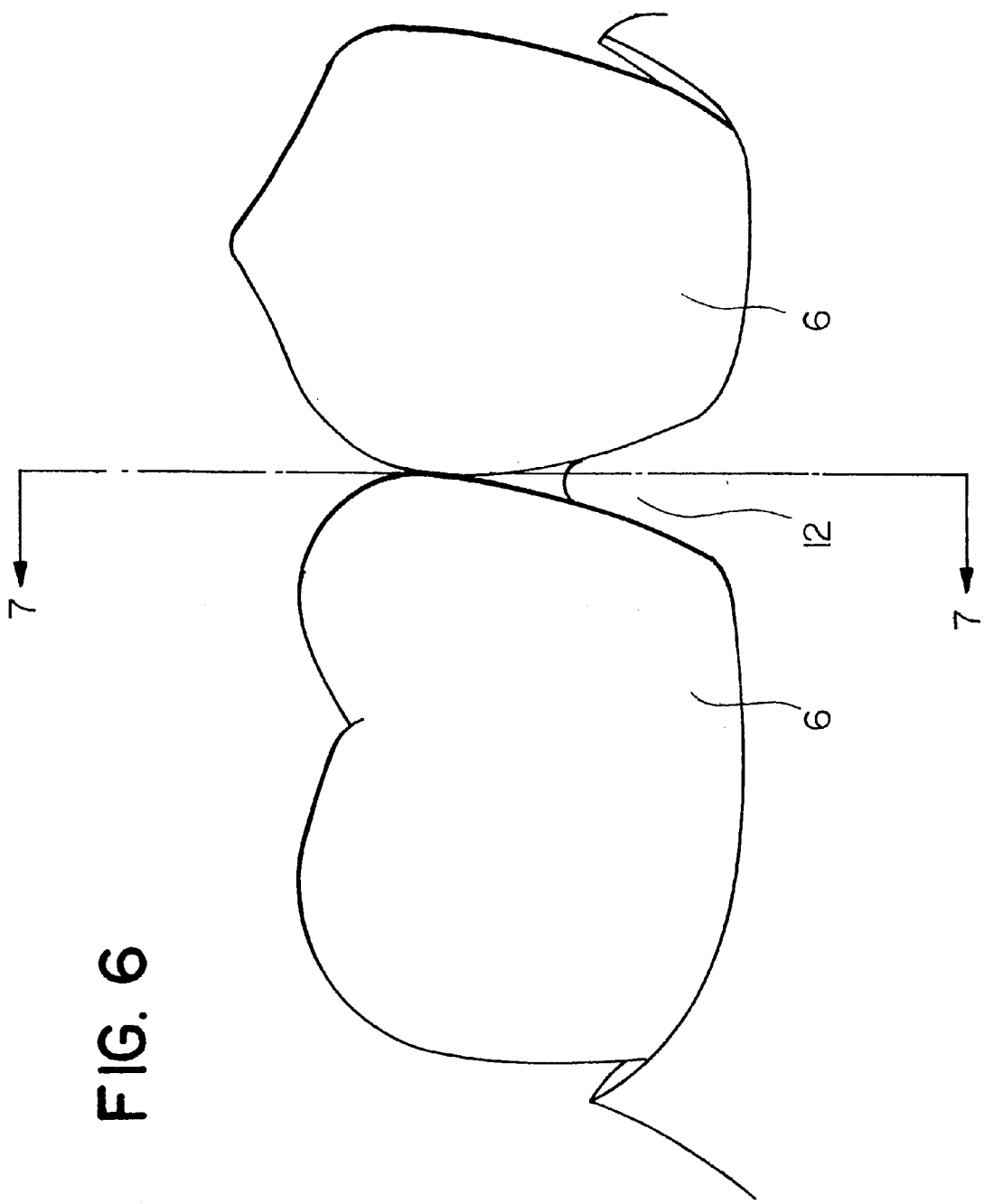
FIG. 6 is lateral perspective of dental contact showing reference for FIG. 7.
Figure 7:
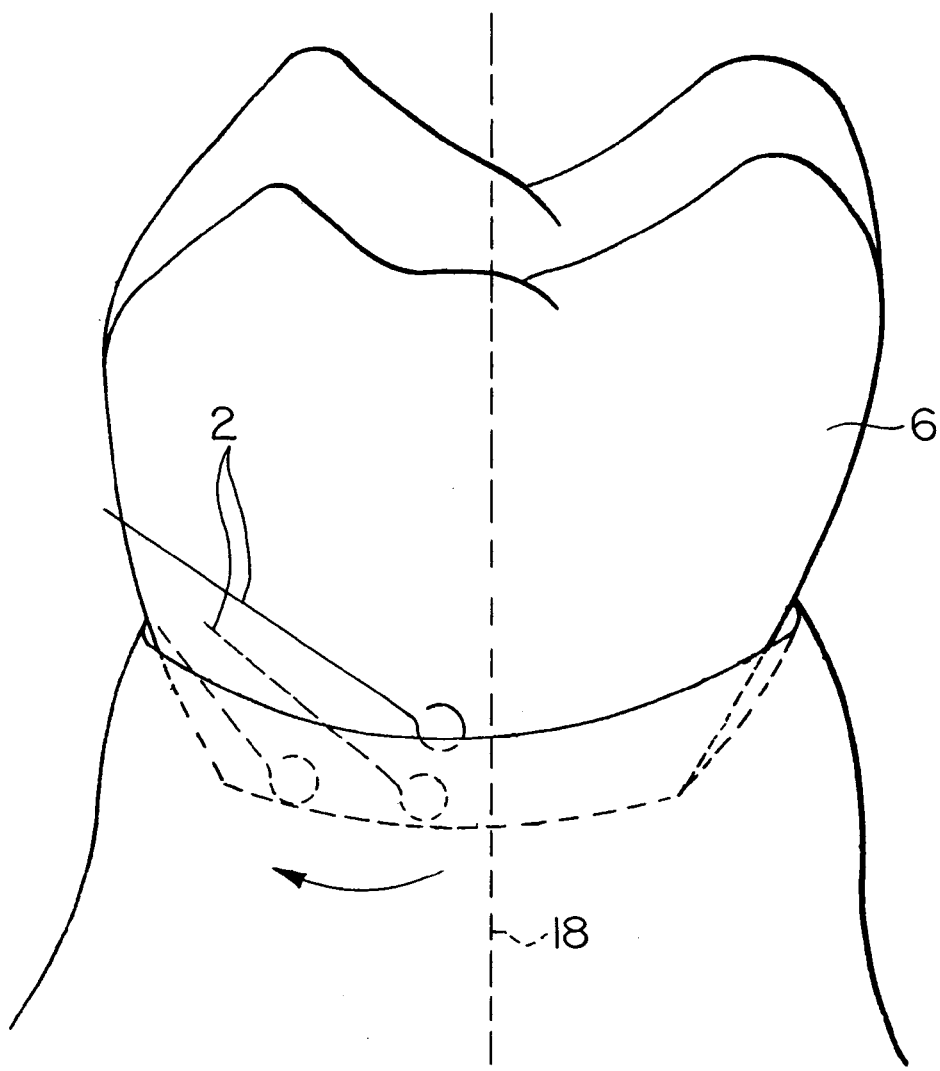
FIG. 7 is a frontal view of molar showing placement of tip ends in sulcus.
Figure 8:
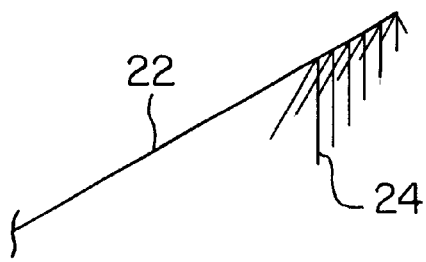
FIG. 8 is a lateral perspective view of stimulator with common wire base.
Figure 9:
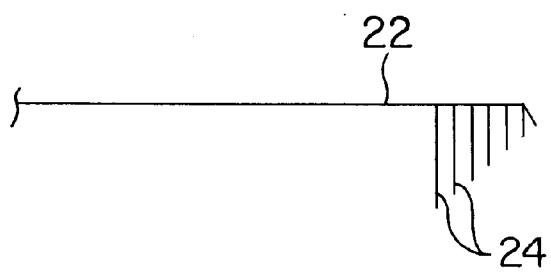
FIG. 9 is a lateral view of stimulator with wire base.
Figure 10:
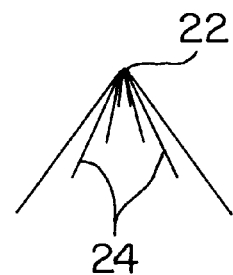
FIG. 10 is an end, or frontal, view of bristles held in a wire base.

Bristles are made longer on the narrow and closed end of vee, FIGS. 1 and 3. This narrow part of the vee is positioned nearer the incisal. The longer bristles allow a deeper reach in the areas furthest away, near the top of the alveolar crest. FIG. 6 shows a buccal lateral view of a contact area between two teeth, 6. FIG. 6 also depicts a cross section view illustrated in FIG. 7. FIG. 7 reveals that longer bristles placed nearest the incisal portion of vee are necessary to reach into the mid-interdental area, 18. Going away from this mid-interdental point, 18 will be closer to the handle and require shorter bristles. Shorter bristles are found on the wider and open end of the vee.

In use, the stimulator of the present invention, 10, is held by hand and free ends of fibers, 2, are placed by feel against the interproximal papillary areas, FIGS. 4 and 5. A small circular motion of the handle is initiated while placing a gentle force in the direction of interproximal sulcus. When the user is satisfied the area is stimulated sufficiently, it is withdrawn directly and applied to the next interdental area.

In the case of the preferred embodiment of parallel bristles attached to a common base, left and right reverse patterns of the vee are necessary. These inverse patterns would accommodate specific areas of the mouth. For example, a normal patterned upright vee would stimulate maxillary right buccal and maxillary left lingual interproximal areas. On a similar base and handle, an inverse mounted vee would stimulate maxillary right lingual and maxillary left buccal areas.

The ends of bristles can terminate in straight traditional nylon tips. The terminal ends can also end in specific stimulating designs, such as paddles or loop designs, application Ser. Nos. 60/025,654 and 08/914,164.

The working ends of bristles could also be replaced by thin segments of pliable rubber. These pieces of rubber would target the same areas and simulate the same interproximal travel as the bristle ends. They are thin enough to enter into the sulcular area and soft enough to conform to the position of the epithelial attachment.

Half of the vee fibers may be removed from the stimulator. This would be advantageous when a singular periodontal defect is present and needs specific consideration.

Conclusions, Ramifications and Scope of Invention

So it can be seen by the reader that the invention disclosed herein is an efficient dental instrument for stimulating the gingiva. It differs from other present day devices because it has all of the following advantages:

It stimulates deep interdental soft tissue—this area is inaccessible to toothbrushes.

It's bristles' ends are held in a vee configuration—corresponding to sulcular anatomy.

The stimulator does not have to pass through a dental contact area—this is the biggest deterrent to regular flossing.

The unique feeling of actually massaging gums in an efficient method will encourage its use on a regular basis.

The present disclosure will therefore make it easier for people to maintain oral health and users would thus be less susceptible to periodontitis and tooth decay.

Mending maladies of mastication is a common experience for most of us. And yet, many oral diseases are preventable.

Professional prophylaxis are performed too often. Complete dental health maintenance should be incorporated into daily practice.

The specific mission of this disclosure is to avail an improved instrument which enables individuals to accomplish self maintenance of oral tissues at a higher level.

Having thus fully described the construction and combination or arrangement of the several parts of my invention, its advantages, and the manner of using the same, what I claim as new is:

1. An interproximal gingival stimulator and cleaner for use in areas between a tooth and interproximal gingival papilla, comprising:

an elongated handle having a proximal end, a distal end, and upper surface and a lower surface;

a plurality of fibers attached to and extending from the upper surface of the distal end of the handle, the fibers having a predetermined length and being arranged such that their free ends generally form a "V" shaped pattern and which generally conforms to the shape of the interdental papilla;

the fibers being further arranged such that those forming the narrow convergent portion of the "V" shaped pattern extend farther outwardly from the handle than the rest of the fibers, and further being arranged such that the fibers gradually shorten in length from the narrow convergent portion of the "V" to the ends of the "V", such that a graduated transition is formed between the longer and shorter fibers.

2. The device of claim 1, wherein the ends of the fibers terminate in a paddle shape.

3. The device of claim 2, wherein the fibers are formed of rubber.

* * * * *